US006638277B2

(12) United States Patent
Schaefer et al.

(10) Patent No.: US 6,638,277 B2
(45) Date of Patent: Oct. 28, 2003

(54) TUMOR ABLATION NEEDLE WITH INDEPENDENTLY ACTIVATED AND INDEPENDENTLY TRAVERSING TINES (75) Inventors: Dean A. Schaefer, Aliso Viejo, CA (US); David Paulk, Hopedal, MA (US); John Sherry, Watertown, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/897,483

(22) Filed: Jul. 2, 2001

(65) Prior Publication Data

US 2002/0072742 A1 Jun. 13, 2002

Related U.S. Application Data (60) Provisional application No. 60/216,198, filed on Jul. 6, 2000.

(51) Int. Cl.[7] .............................................. A61B 18/18
(52) U.S. Cl. ............................ 606/41; 606/34; 607/101
(58) Field of Search ............................ 606/32–34, 41, 606/47–50; 607/101, 102, 115, 116

(56) References Cited

U.S. PATENT DOCUMENTS

| 5,370,675 | A | * | 12/1994 | Edwards et al. ............... 606/32 |
| 5,536,267 | A | * | 7/1996 | Edwards et al. ............... 606/41 |
| 5,672,173 | A | | 9/1997 | Gough et al. |
| 5,672,174 | A | | 9/1997 | Gough et al. |
| 5,728,143 | A | | 3/1998 | Gough et al. |
| 5,741,225 | A | | 4/1998 | Lax et al. |
| 5,766,153 | A | * | 6/1998 | Eggers et al. ............... 604/114 |
| 5,782,827 | A | | 7/1998 | Gough et al. |
| 5,800,484 | A | | 9/1998 | Gough et al. |
| 5,810,804 | A | | 9/1998 | Gough et al. |
| 5,827,276 | A | | 10/1998 | LeVeen et al. |
| 5,855,576 | A | | 1/1999 | LeVeen et al. |
| 5,863,290 | A | | 1/1999 | Gough et al. |
| 5,868,740 | A | * | 2/1999 | LeVeen et al. ............... 606/41 |
| 5,913,855 | A | | 6/1999 | Gough et al. |
| 5,925,042 | A | | 7/1999 | Gough et al. |
| 5,928,229 | A | | 7/1999 | Gough et al. |
| 5,935,123 | A | | 8/1999 | Edwards et al. |
| 5,951,547 | A | | 9/1999 | Gough et al. |
| 5,954,717 | A | | 9/1999 | Behl et al. |
| 5,980,517 | A | | 11/1999 | Gough et al. |
| 6,041,260 | A | | 3/2000 | Stern et al. |
| 6,050,992 | A | | 4/2000 | Nichols |
| 6,053,937 | A | | 4/2000 | Edwards et al. |
| 6,059,780 | A | * | 5/2000 | Gough et al. ............... 606/41 |
| 6,071,280 | A | | 6/2000 | Edwards et al. |
| 6,077,261 | A | | 6/2000 | Behl et al. |
| 6,080,149 | A | | 6/2000 | Huang et al. |
| 6,080,150 | A | | 6/2000 | Gough et al. |
| 6,090,105 | A | | 7/2000 | Zepeda et al. |
| 6,235,023 | B1 | * | 5/2001 | Lee et al. ............... 606/41 |

FOREIGN PATENT DOCUMENTS

WO    WO 00/13602 A    3/2000

OTHER PUBLICATIONS

Radiofrequency Energy: Clinical Applications (Radio Therapeutics Corporation Apr. 9, 1999).

RTC Training Manual—Chapters 1–9 (Radio Therapeutics Corporation Jun. 1, 1998).

(List continued on next page.)

Primary Examiner—Michael Peffley
(74) Attorney, Agent, or Firm—Bingham McCutchen LLP (57) ABSTRACT The present invention relates to an apparatus and method for utilizing energy, such as radio frequency (RF) energy, to treat defined areas of tissue and more particularly to ablate tumors with RF energy through the use of a needle having a spreading array of individually traversing conductive tines which are independently positioned and activated.

31 Claims, 4 Drawing Sheets

OTHER PUBLICATIONS

Radiotherapeutics Corporation, "Radiofrequency Energy: Clinical Applications—Previously presented data from experiences with the RF 2000™ Generator and the LeVeen™ Needle Electrode" 1. Abstract: Soulen, et al, "Oral Presentation at the SCVIR," Mar. 20–15, 1999, in *Radiofrequency Energy: Clinical Applications,* Radio Therapeutics Corporation.

Radiotherapeutics Corporation, "Radiofrequency Energy: Clinical Applications—Previously presented data from experiences with the RF 2000™ Generator and the LeVeen™ Needle Electrode" 2. Abstract: Bauer et al., "Radiofrequency Ablation Therapy for Large, Complex Hepatic Metastases," $52^{nd}$ Annual Mtg. of Society of Surgical Oncologist, Mar. 4–7, 1999, in *Radiofrequency Energy: Clinical Applications,* Radio Therapeutics Corporation.

Radiotherapeutics Corporation, "Radiofrequency Energy: Clinical Applications—Previously presented data from experiences with the RF 2000™ Generator and the LeVeen™ Needle Electrode" 3. Abstract: Birdwell et al., "Preliminary Experience with Intraoperative Radiofrequency Breast Tumor Ablation," $84^{th}$ Annual Mtg. of the Radiology Society of North America, Nov. 29–Dec. 4, 1998 in *Radiofrequency Energy: Clinical Applications,* Radio Therapeutics Corporation.

Radiotherapeutics Corporation, "Radiofrequency Energy: Clinical Applications—Previously presented data from experiences with the RF 2000™ Generator and the LeVeen™ Needle Electrode" 4. Abstract: Curley et al., "Freeze or Fry: A Comparison of Cryoablation and Radiofrequency Ablation for Malignant Liver Tumors," 49the Annual Mtg. of the American Association for the Study of Liver Diseases, Nov. 6–Nov. 10, 1998 in *Radiofrequency Energy: Clinical Applications,* Radio Therapeutics Corporation.

Radiotherapeutics Corporation, "Radiofrequency Energy: Clinical Applications—Previously presented data from experiences with the RF 2000™ Generator and the LeVeen™ Needle Electrode" 5. Abstract: Gantert et al., "Radiofrequency Ablation of Malignant Liver Tumors: Development of a New Multi–Array Electrode and Results of the First Human Treat–and–Resect Trials," $51^{st}$ Annual Mtg. of the Society of Surgical Oncologists, Mar. 26/Mar. 29, 1998 in *Radiofrequency Energy: Clinical Applications,* Radio Therapeutics Corporation.

Radiotherapeutics Corporation, "Radiofrequency Energy: Clinical Applications—Previously presented data from experiences with the RF 2000™ Generator and the LeVeen™ Needle Electrode" 6. Abstract: Gandhi et al., "MR–Guided Radio Frequency Ablation of Breast Tissue Preliminary Results in a Mixed Fat/Water Tissue Phantom," $23^{rd}$ Annual Mtg. of Society of Cardiovascular & Interventional Radiologists, Feb. 28–Mar. 5, 1998.

Radiotherapeutics Corporation, "Radiofrequency Energy: Clinical Applications—Previously presented data from experiences with the RF 2000™ Generator and the LeVeen™ Needle Electrode" 7. Abstract: LeVeen et al., "Large RF Ablation Lesion Produced with a Radially Expanding Monopolar Array Electrode: Long–term Porcine Experiments," $22^{nd}$ Annual Mtg. of Society of Cardiovascular & Interventional Radiology, Mar. 8–13, 1997.

Radiotherapeutics Corporation, "Radiofrequency Energy: Clinical Applications—Previously presented data from experiences with the RF 2000™ Generator and the LeVeen™ Needle Electrode" 8. Abstract: LeVeen et al., "Large–Volume Porcine Liver Ablation with Use of a Percutaneous Expandable Electrosurgical Probe," $21^{st}$ Annual Mtg. of Society of Cardiovascular & Interventional Radiology, Mar. 2–Mar. 7, 1996.

Radiotherapeutics Corporation, "Radiofrequency Energy: Clinical Applications—Previously presented data from experiences with the RF 2000™ Generator and the LeVeen™ Needle Electrode" 9. Curley, "Case Study: Radiofrequency–induced necrosis of liver tissue—Nectoris zones 1 and 6 months after the procedure."

Curley, "Radiofrequency Ablation of Unresectable Primary and Metastatic Hepatic Malignancies", Anals of Surgery, pp 1–8: 130(1), 1999.

LeVeen, "Laser Hyperthermia and Radiofrequency Ablation of Hepatic Lesions," Seminars in Interventional Radiology, pp 313–324: 14 (3), 1997.

* cited by examiner

TUMOR ABLATION NEEDLE WITH INDEPENDENTLY ACTIVATED AND INDEPENDENTLY TRAVERSING TINES

CROSS-REFERENCE TO RELATED APPLICATIONS

This application claims the benefit of U.S. Provisional Application No. 60/216,198, filed Jul. 6, 2000.

BACKGROUND OF THE INVENTION

1. Field of the Invention

The present invention generally relates to an apparatus and method for utilizing energy, such as radio frequency (RF) energy, to treat defined areas of tissue and more particularly to ablate tumors with RF energy through the use of a needle having a spreading array of individually traversing conductive tines which are independently positioned and activated.

2. Description of Related Art

Radio frequency energy has been used in medical procedures for many years for the treatment of soft tissue. Radio frequency ablation occurs from a high frequency alternating current flowing from the tip of an electrode through the surrounding tissue. Ionic agitation is produced in the tissue around the electrode tip as the ions attempt to follow the change in direction of the alternating current. This ionic agitation creates frictional heating of the tissue around the electrode. Thus, similar to a microwave, the tissue heats even though the electrode does not; although conducted heat may progress back to the electrode from the surrounding tissue. The heat generated results in local cell coagulation and necrosis. Coagulated cells die and thus cease dividing. This technology has been used for example in the treatment of unresectable hepatic cancer.

RF ablation may be performed through an open abdominal incision or via laparoscopy which is performed through multiple, small skin incisions. If indicated, RF ablation can also be conducted percutaneously through small skin incisions. The duration of the procedure depends on many factors, including the number of applications desired and the location of the tissue to be treated. Typically, the procedure will be performed in a surgical suite where the patient can be monitored by imaging equipment.

RF ablation has had very promising results in the treatment of hepatic cancer. Using devices in the prior art, the procedure, however, takes a considerable amount of time, approximately 15 minutes for every 4 centimeters of tumor after the needle has been placed in the patient and the tines fully deployed. A clinical investigation of RadioTherapeutics is discussed in Curley et al., *Radiofrequency Ablation of Unrectable Primary and Metastatic Hepatic Malignancies*, 230 ANNALS OF SURGERY 1 (1999), which is incorporated herein by reference in its entirety.

A device that is currently on the market, the "LeVeen Needle Electrode" by RadioTherapeutics Corporation, deploys an umbrella of 10 tines which burrow into the tumor growth distributing the RF energy thereby heating and destroying the cells. Following the procedure, the body reabsorbs the destroyed cells over a period of time. Structurally, the LeVeen Needle Electrode consists of ten evenly spaced wires that are deployed through an insulated metal cannula. When deployed, the array of wires advances through the tissue in a constant radius curve away from the metal cannula, producing the umbrella shaped design of the LeVeen Needle Electrode. The cannula supports the array which is deployed within its predetermined shape and dimensions. According to marketing literature, this allows penetration of the tissue irrespective of density. Thus, the wires of the LeVeen Needle Electrode supposedly can be deployed into tissue which is hard, such as calcified tissue in its entirety. RadioTherapeutics marketing literature also states that U.S. Pat. Nos. 5,827,276, 5,855,576, and 5,868,740 describe the Le Veen Needle, each of which is incorporated herein by reference.

Figure 1:
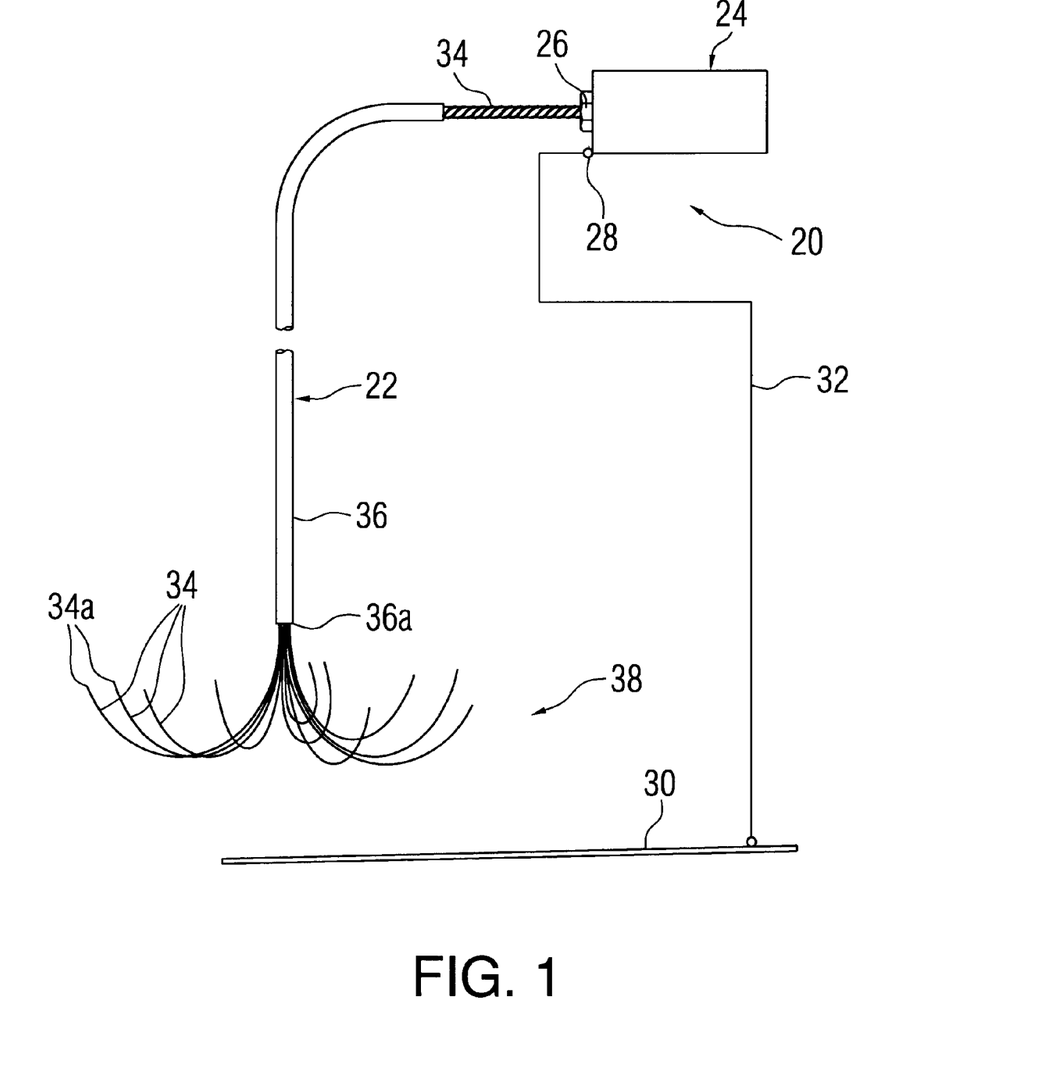
FIG. 1 illustrates a tissue treatment apparatus currently known in the art.

FIG. 1 depicts one version of the Le Veen Needle 20 in accordance with the prior art which includes insertion device 22 electrically connected to a radio frequency generator 24. The radio frequency generator 24 includes at least one active terminal 26 and a return terminal 28 with ground plate 30 electrically connected by conductor 32 to terminal 28. Insertion device 22 is comprised of a plurality of electrically conductive wires 34 which are bundled at a proximal end and connected to terminal 26 to conduct RF current therefrom. Wires 34 are threaded through an electrically insulated or non-conductive tube or catheter 36.

As shown in FIG. 1, a 10-wire array 38 is formed with each wire 34 arching from catheter 36 in a general "U" shape with each wire substantially uniformly separated. Thus, array 38 is formed of a plurality of wires 34 curving radially outwardly from the axis of distal end 36a of catheter 36. Wires 34 all extend a length such that, when fully extended past catheter distal end 36a, a portion of each wire 34 is perpendicular to the axis of tube 36 and which continue to curve back and up such that wire distal ends 34a are oriented generally parallel to the axis of the tube distal end 36a. Wire distal ends 34a thus remain uniformly deployed and separated within a plane orthogonal to the tube distal end 36a.

In addition, use of the LeVeen Needle Electrode creates a roughly spherical lesion which is approximately equal to the diameter of the fully deployed wire array. Thus, a 3.5 cm LeVeen Needle Electrode will produce a thermal lesion approximately 3.5 cm in diameter. RF energy radiates from individual array wires into adjacent tissue in a 360 degree pattern. Each wire is also connected to the same power source. The energy level, and thus the heating effect, falls off rapidly at increasing distance from the individual wires. The highest temperature will therefore always be created immediately adjacent to the wires. In addition, tissue heat can be conducted up a short distance of the cannula which results in a slight peaking of the thermal lesion around the cannula. This results in a thermal lesion which is spherical around the tines of the array and slightly sloped up the shaft of the cannula. The center of the spherical lesion is centered on the array and therefore slightly offset distally from the end of the cannula.

The major disadvantage of such devices is that the tines cannot be adjusted individually to fit the volumetric dimensions of the tumor or tissue area to be treated. Each tine must be deployed or withdrawn concomitantly. Thus, if a tumor is irregularly shaped, the device may have to be inserted several times at different locations and at different depths in order to treat the entire volume of tissue. This increases the time to perform the procedure as well as increasing the risk of patient complications.

Radio Therapeutics literature also indicates that the RF generator used in conjunction with the Levine Needle was designed to respond to changes in tissue impedance and to detect changes in bulk tissue impedance throughout the target volume of tissue. Controlled application of RF energy from a shaped array with many wires allegedly causes relatively uniform desiccation of the tissue with a subsequent increase in tissue impedance. The rise in impedance that occurs following the application of power for a designated period of time indicates that thermal ablation has occurred. One disadvantage, however, is that the tissue treated tends to overheat too quickly thereby destroying the cells and desiccating the area immediately surrounding each tine. When this occurs, impedance is greatly increased and flatlines. Once the impedance level flatlines, depth ablation is no longer possible and the affective zone is moved proximally along the tine toward the cannula or in conventional LeVeen needle technology goes to a tine with the least resistance. Once the small area surrounding the needle is completely desiccated, the needle must be repositioned which again increases procedural time and the chance of patient complications. RF generators, such as the RF 2000 Radiofrequency Generator, by RadioTherapeutics Corporation, is described in U.S. Pat. Nos. 5,817,092, 5,827, 276, 5,855,576, and 5,868,740, each of which is incorporated herein by reference in its entirety.

SUMMARY OF THE INVENTION

The present invention includes an improved method and apparatus in the form of a tumor ablation needle with individually traversing tines used to transmit energy, such as RF energy, in order to ablate and dessicate various areas of tissue, in which said tines can be positionally adjusted to the dimensions of the target area thereby increasing the affective desiccation area and reducing procedural time.

The present invention also includes an improved method and apparatus in the form of a tumor ablation needle with tines that are periodically and independently activated to reduce dessication of the ablation area, thereby reducing impedance and increasing the radius and depth of energy penetration.

The present invention also includes the application of such methods and needles to ablate or dessicate any lesion, tumor, lump, node, or other defined or undefined area of tissue, bone, or other living or nonliving matter.

In one embodiment, the present invention comprises a tumor ablation needle with individually traversing tines which can be independently extended or retracted. Thus, if the needle is placed close to the wall of a tumor, the extension of tines adjacent to the wall can be limited while the tines distant from the wall can be traversed as deep as necessary. This increases the affective ablation area and reduces the time to dessicate the entire tumor because it reduces the potential need for repositioning the needle into the tumor in order to dessicate the entire region of tissue.

In another embodiment, the present invention comprises an alternative means of delivering the active electrodes to each individual tine in an attempt to decrease impedance and increase the radius and depth of energy (such as RF energy) penetration and dessication. This concept is analogous to an electrical distributor of an automobile. A center source of power delivers the active electrode through a rotating single, double, or multiple node design with each contact being connected directly to an individually insulated tine that travels through the lumen of the needle device. Thus, each tine is activated individually as the active electrode rotates about its axis. In the dual node design opposite contacts of the distributor would receive the active electrode which would translate to opposite ends of the tumor ablation sight being desiccated. The initial spike in heat and impedance would be allowed to dissipate in the cells surrounding each tine as it waits for its next active electrode.

BRIEF DESCRIPTION OF THE DRAWINGS

The various advantages and novel features of this invention will be more fully apparent from a reading of the Detailed Description of the Present Invention in conjunction with the accompanying drawings in which like reference numerals refer to like parts, and in which.

DETAILED DESCRIPTION THE PRESENT INVENTION

The present invention provides an improved method and apparatus in the form of a tumor ablation needle with individually traversing tines used to heat, ablate and dessicate various tumors or areas of tissue. In addition, the present invention provides a method and apparatus whereby the tines are periodically and independently activated to prevent overheating of the ablation area, thereby reducing impedance and increasing the radius and depth of energy penetration and dessication.

In accordance with the present invention, the following examples are specific embodiments of the tumor ablation apparatus, RF distributor apparatus, and methods of using the same. However, it is to be understood that these embodiments are presented by way of example only. It is expected that others will perceive and practice variations which, though differing from the following, do not depart from the spirit and scope of the invention as described and claimed herein.

In one embodiment, the present invention utilizes a plurality of independent tissue-penetrating electrodes, typically in the form of sharpened, small diameter metal wires or tines which can penetrate into tissue as they are advanced from the cannula. The electrodes may also be in the form of blades, helices, screws, and other similar objects, materials and shapes. The electrode tines of the present invention are independent and can be adjusted to the dimensions of the target area thereby increasing the affective desiccation area and reducing procedural time.

Before introduction into tissue, the electrode tines are radially retracted or otherwise remain in a constrained configuration. Thereafter individual tines can be advanced into the tissue by an actuator mechanism to achieve the desired three-dimensional area to be treated. The electrode tines may extend in a straight, curved, or irregular line from the distal end of the cannula. In one embodiment each tine is configured and dimensioned such that the distal ends of each tine substantially conform to an outwardly everted configuration when extended beyond the distal end of the elongated member and in a radially constrained configuration when axially retracted back within the elongated member. In a more specific embodiment, the electrode tines will diverge radially outwardly from the cannula in a uniform pattern, i.e. with the spacing between adjacent electrodes diverging in a substantially uniform and/or symmetric pattern. Various other tine divergence patterns, dimensions and configurations are also encompassed by the present invention.

The electrode tines may be constructed of conductive metals having resilience and shape-retaining properties such as stainless steel, nickel-titanium alloys, spring steel alloys, and similar metals. Alternatively, the tines may be constructed of material which does not have shape-retaining properties in which case some deflection element or mechanism could be provided on the elongated member to deflect the tines in a desired three-dimensional pattern. In one embodiment, the tines will be sharpened at their distal ends to enhance their ability to penetrate tissue and may be strengthened using standard heat treatment and other metallurgical processes. In another embodiment, the tines may have circular cross-sections with various diameters but such diameters will preferably range from about 0.1 mm to about 2 mm and preferably from about 0.2 mm to about 0.5 mm. Alternatively, the tines may have non-circular cross-sections with analogous dimensions.

The electrode tines will be contained within an elongated member which incorporates the cannula or other delivery element which is constructed of a rigid material such as metal or plastic. The elongated member functions to constrain the individual electrode elements in a radially-collapsed configuration to facilitate their introduction to the tissue target site. In one preferred embodiment of the present invention, the elongated member contains a number electrically insulated elongated inner tubes, shafts, or conduits extending axially therethrough. Each inner tube, shaft, or conduit contains a lumen. The elongated member itself may be solid or hollow (in which case the elongated member would contain a primary lumen).

The inner tubes, shafts, or conduits (collectively referred to herein as the "inner tubes") extend from the proximal region of the elongated member to the distal end of the cannula or delivery element. Each of said inner tubes contains an elongated individual electrode tine. Alternatively, the inner tube is not an independent conduit or shaft but rather an insulative jacket which insulates the individual tines. In one embodiment, the electrode tines may be insulated and coiled (or otherwise compacted) at the proximal end of the elongated member before entering the inner tubes. This allows the tine enough slack to be retracted within or extended from the distal end of the elongated member. The tines at the distal end of the elongated member are preferably uninsulated.

A component or element may also be provided for introducing the elongated member to the target site within the treatment region to be treated. For example, a conventional sheath and sharpened obturator (stylet) assembly can be used to initially access the target site. The assembly can be positioned under ultrasonic or other conventional imaging, with the obturator/stylet then being removed to leave an access lumen through the sheath. The electrode tines can then be introduced through the sheath lumen while constrained in the elongated member. The electrode tines are then individually extended distally beyond the distal end of the sheath into the treatment region of tissue. The obturator may be removed from the sheath in order to accept the elongated member. Alternatively, the introducer may comprise a self penetrating element at the distal end of the elongated member.

Figure 2:
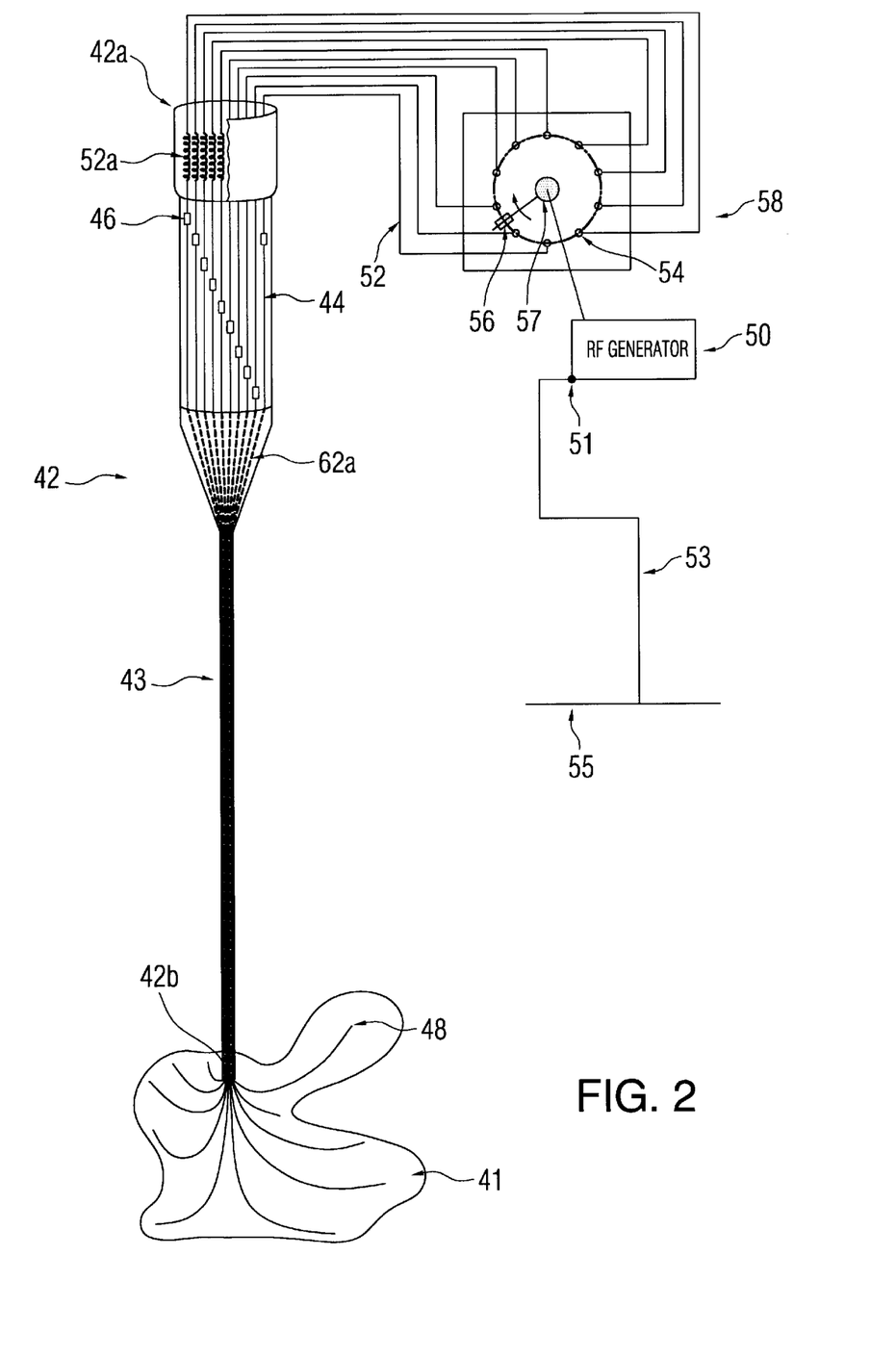
FIG. 2 illustrates a tissue treatment apparatus with independently traversing tines.
Figure 3:
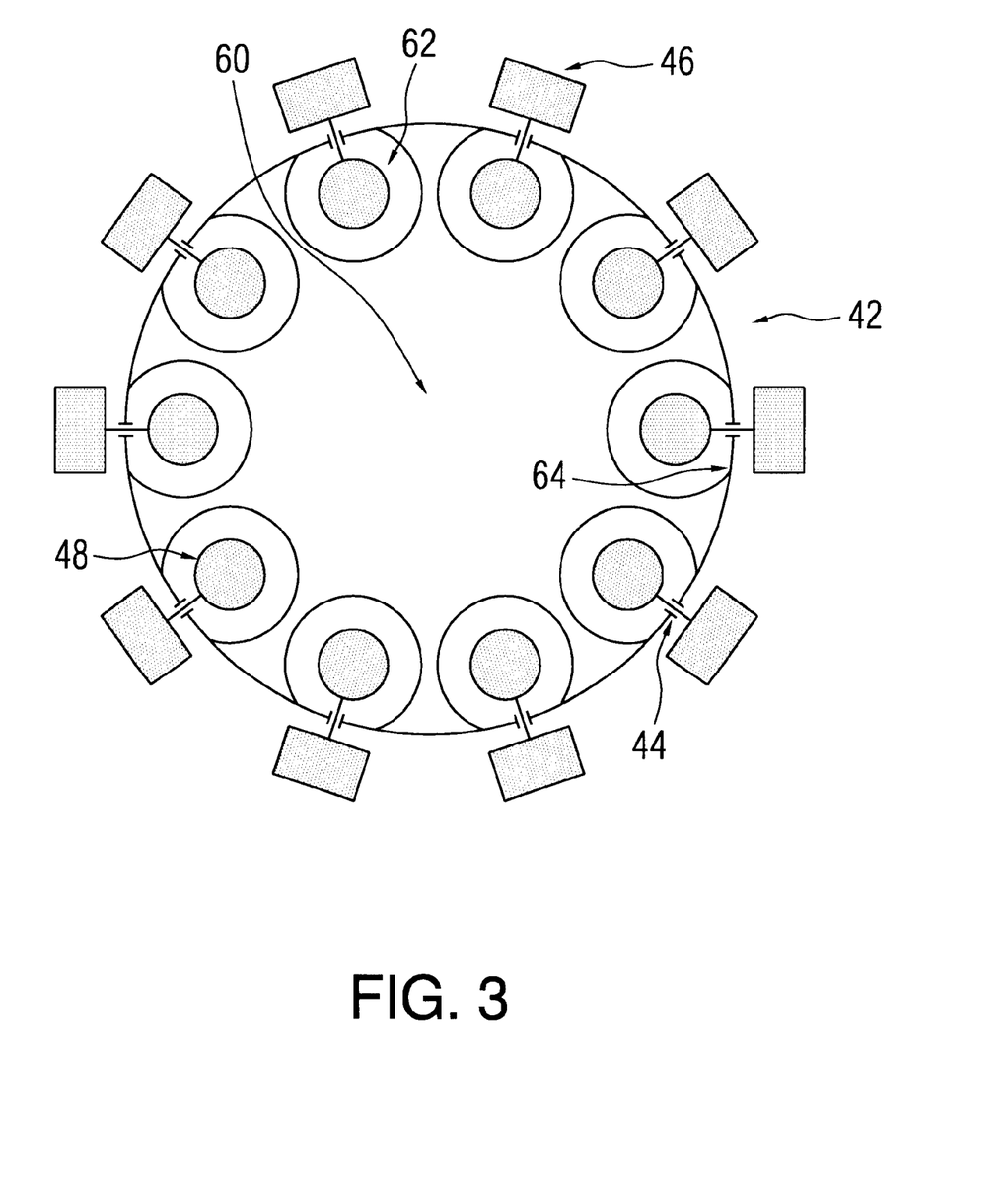
FIG. 3 illustrates a cross sectional view of the tissue treatment apparatus of FIG. 2.

In a more specific embodiment, FIG. 2 and FIG. 3 illustrate an apparatus for volumetric tumor ablation in accordance with the present invention which includes an electrically insulated elongated member 42 having a proximal end 42a and distal end 42b. The elongated member and different portions thereof may be constructed of any material including metal and plastic and may be of any dimension. In one embodiment the length of the elongated member is from about 5 cm to about 40 cm, the diameter of the distal end is from about 1 mm to about 3 mm, and the diameter of the proximal end is from about 10 mm to about 50 mm. In one particular embodiment, the elongated member incorporates cannula 43 and contains a primary lumen 60 and multiple electrically insulated inner tubes 62 each containing a separate lumen which axially traverse elongated member 42 from proximal end 42a to distal end 42b. The inner tubes may each be directly attached to the inner wall 64 of elongated member 42. In other embodiments, the inner tubes may be separate from inner wall 64 and/or connected to other inner tubes. Alternatively, inner tube 62 does not need to be an independent conduit for tine 48 to traverse through. Inner tube 62 may simply be an insulative jacket attached to tine 48 and attached or unattached to member 42.

The inner tubes extend down to the distal end of the elongated member through the cannula as represented by the dashed lines 62a. The diameter of each inner tube 62 may vary but is preferably from about 0.1 mm to about 1 mm. Each inner tube 62 insulates or contains an independent electrode tine 48. The electrode tines are generally sharpened, small diameter metal wires which can penetrate into tissue as they are advanced from the cannula and may also be in the form of blades, helices, screws, and other similar objects, materials and shapes. The tines may be constructed of conductive metals having resilience and shape-retaining properties such as stainless steel, nickel-titanium alloys, spring steel alloys, and similar metals. In one embodiment, the electrode tines are insulated 52 at the proximal end of the elongated member 42a where the tines may be coiled or otherwise compacted 52a in the inner tube 62 or before entering the inner tube. This allows each tine enough slack to be retracted in or extended out from cannula 43 at the distal end of the elongated member 42b. Alternatively, the electrode tines may simply be insulated and coiled or compacted at any point inside elongated member 42 to provide the slack necessary to retract or extend the tines from the distal end of elongated member 42b.

The proximal terminal end of each tine is connected to an independent electrode terminal element 54 in an RF distributor 58 connected to a radio frequency generator 50 in which said elements are periodically contacted by an active rotating electrode 56 which provides radio frequency energy in cyclic intervals. The radio frequency distributor 58 includes a plurality of independent electrode terminal elements 54 corresponding to the number electrode tines 48. The active rotating electrode may be uniformly or evenly cycled among the tines or may dwell longer at one particular tine(s) or terminal element(s). For example, the active rotating electrode may contact one tine for a longer duration than another tine during its cycle. A return terminal 51 of RF generator 50 with ground plate 55 electrically connected by conductor may also be included.

In one embodiment, the elongated member 42 has apertures 44 which extend axially along a portion of the exterior wall of the elongated member into each of the electrically insulated inner tubes 62. The width of each aperture may vary but is generally from about 50 $\mu$m to about 500 $\mu$m. Extending through a portion of each aperture 44 into the inner tube 62 and connected to each electrode tine 48 is an actuator 46. Alternatively, the actuator can be connected directly to the electrode tine where there is no inner tube and/or where the tines are simply insulated with an insulative jacket. The actuator can be moved to extend or retract each tine from the distal end of the cannula 42b in order to substantially treat the entire area of an irregularly shaped tumor 41. The actuator can be constructed of any material and may consist of a side member such as an arm which extends through aperture 44 from the exterior surface of the elongated member 42 and is attached to a portion of the electrode tine 48. The actuator may be pushed, pulled or otherwise moved to extend or retract each individual tine from the distal end of the elongated member.

RF current can be applied through the electrodes in a monopolar or bipolar fashion. In one embodiment, the RF power supply may be a conventional general purpose electrosurgical power supply operating at a frequency in the range from about 400 kHz to about 1.2 MHZ, with a conventional sinusoidal or non-sinusoidal wave form. Such power supplies are available from many commercial suppliers, such as RadioTherapeutics, Valleylabs, Aspen, Bovie, and Birtcher.

In another embodiment, the RF power supply may be in the form of an RF generator and distributor which provides RF current to the individual tines in cyclic intervals. The RF current may be uniformly or evenly cycled among the tines or may be cycled to provide more or less RF current to a particular tine or tines. Similar to a microwave set on defrost, RF current is turned on and off with respect to each tine. This allows the initial heat or energy to dissipate in the cells surrounding each tine before receiving more RF energy thereby reducing the problem of overheating and tissue dessication.

Figure 4:
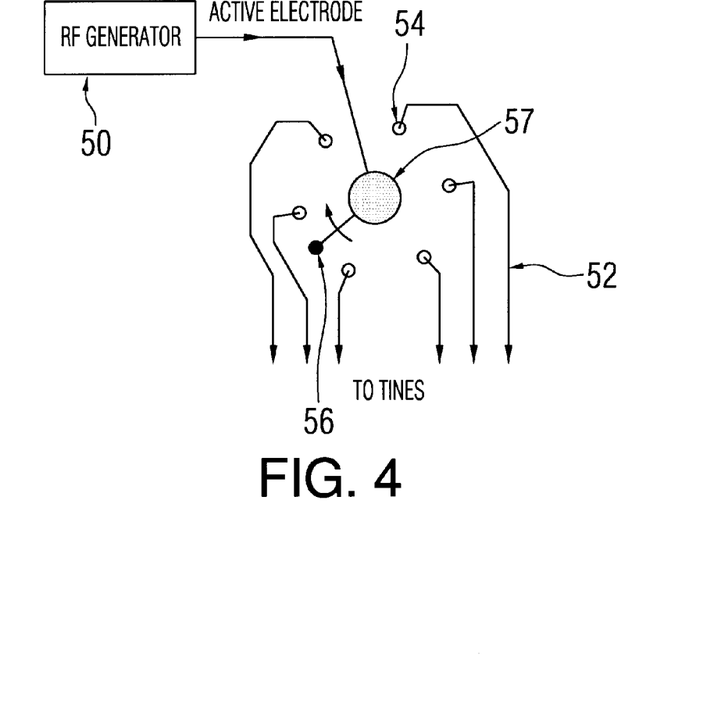
FIG. 4 illustrates a radio frequency distributor with an active rotating electrode of a single node design.

In a more specific embodiment FIG. 4 illustrates a single node design radio frequency distributor including an RF generator 50 which supplies a pivot element 57 with RF energy. Connected to the pivot element is the active rotating electrode containing a single node 56 which distributes the RF energy as it rotates to a number of independent electrode terminal elements 54 which are connected to the individual insulated tines 52.

Figure 5:
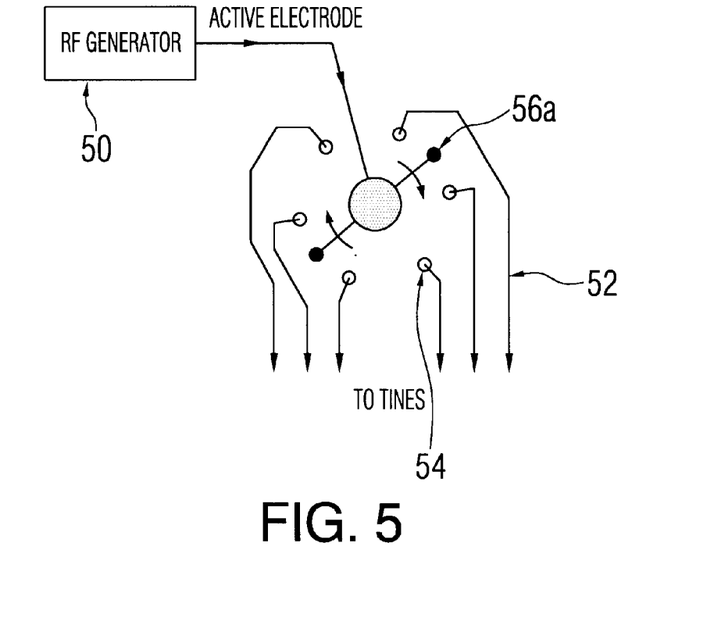
FIG. 5 illustrates a radio frequency distributor with an active rotating electrode of a dual node design.

In another specific embodiment FIG. 5 illustrates a dual node design radio frequency distributor including an RF generator 50 which supplies RF energy to the pivot element 57. Connected to the pivot element is the active rotating electrode containing dual node 56a. The dual node distributes the RF energy as it rotates to a number of independent electrode terminal elements 54 which are connected to the individual insulated tines 52.

The advantage of these novel radio frequency distributors is that each tine is activated individually as the active electrode rotates about its axis. This delivery mechanism maximizes the energy delivered to the tissue with a generator of finite power by minimizing the risk of desiccating the tissue at the tine. The single node design works much like the distributor of an automobile. Because each tine is activated individually the initial spike in energy would be allowed to dissipate in the cells surrounding each tine before the active electrode returns. In one embodiment, the optimal velocity at which the active electrode rotates is generally from about 1 cycles/second to about 100 cycles/second. In the dual node design, opposite contacts of the distributor receive the active electrode which would translate to opposite ends of the tumor ablation sight being desiccated. The dual node design works in a similar manner to the single node design except that the duration between the tine currents would be shorter and therefore the rotational velocity may have to be decreased.

The treatment area itself may be any lesion, tumor, lump, node, or other defined or undefined area of tissue, bone, or matter in a living or nonliving organism. Preferably, the treatment area will be a solid tumor that is located in the organ of a patient such as the liver, kidney, pancreas, breast, prostate, intestine, bladder, colon, or other organ. The volume of the tumor or tissue to be treated may be of any size but typically includes a total volume from 1 cm$^3$ to 150 cm$^3$, usually from 1 cm$^3$ to 50 cm$^3$, and frequently from 2 cm$^3$ to 35 cm$^3$. The shape and dimensions of the tumor or tissue may be spherical, ellipsoidal, asymmetrical, or irregularly shaped and may be identified using high resolution ultrasound which can be used to monitor the size and location of the tumor or other lesion being treated, either intraoperatively or externally. Ultrasound (US) is often preferred at the time of treatment for probe placement and to monitor lesion development. However, acoustic shadowing does not allow visualization of the distant margins of the lesion. See Robert F. Leveen, *Laser Hyperthermia and Radiofreqency Ablation of Hepatic Lesions,* 14 SEMINARS IN INTERVENTIONAL RADIOLOGY 313, 321–22. Other imaging techniques include magnetic resonance imaging (MRI), computer-assisted tomography (CAT), fluoroscopy, and the use of radio-labeled tumor-specific probes. Dynamic contrast-enhanced CT has been frequently used for post procedure assessment. Dynamic CT scans show the effective treatment area as a well-defined, nonenhancing area, easily distinguished from untreated areas of tissue. Id. In addition, MRI with thermal mapping data collection capability would enable the user to determine where heat sinks are occurring in the targeted tumor. This information would enable the user to adjust tine placement and/or the delivery mechanism of power to deliver more power to the appropriate tine(s) (i.e., through a longer duration of contact with the rotating electrode).

In accordance with the present invention, the following examples are embodiments of specific methods of treating defined areas of tissue with RF energy using the apparatus as described and claimed herein. However, it is to be understood that these embodiments are presented by way of example only. It is expected that others will perceive and practice variations which, though differing from the following, do not depart from the spirit and scope of the invention as described and claimed.

In one embodiment, the elongated member is inserted into the area of tissue to be treated. The treatment area may be a tumor, lump, node, or other defined or undefined area of tissue, bone, or matter in a living or nonliving organism. In one particular embodiment of the present invention, the treatment area is a tumor such as a malignant hepatic tumor. After the elongated member is inserted into the treatment area, the operator of the apparatus may independently deploy each tine to a desired position within the treatment area by pushing, pulling, or sliding the actuator corresponding to a particular tine. The operator may then supply radio frequency energy to each tine by turning on the power to an RF generator, as herein described, which is connected to the proximal end of each tine.

In one embodiment, the RF generator is connected to a distributor which contains an active rotating electrode that supplies each tine with radio frequency energy in cyclic intervals. The active rotating electrode may be evenly cycled among the tines or may contact one or more tines for a longer or shorter period of time. The active rotating electrode may be of a single node design, double node design, or multiple node design. In one particular embodiment the velocity of the active rotating electrode is from about 1 cycles/second to about 100 cycles/second.

In another embodiment, the elongated member is introduced into the tissue percutaneously (through the skin) using an introducer such as an obturator/stylet and sheath assembly. The obturator/stylet and sheath assembly is pushed through the skin until the distal end of the sheath lies at or within the area of tissue to be treated. The obturator/stylet is then withdrawn from the sheath leaving an access lumen to the area of tissue to be treated. The elongated member is then introduced through the access lumen of the sheath so that the distal end of the elongated member lies near the distal end of the sheath. The electrode tines are then independently extended distally from the distal end of the elongated member by pushing, pulling, or sliding the actuator corresponding to a particular tine or tines.

Whereas the invention has been shown and described in connection with specific embodiments hereof, many modifications, substitutions and additions may be made which are within the intended broad scope of the appended claims. Thus, it should be understood that the present invention encompasses the use of other methods and apparatuses for introducing a plurality of elongated independent electrode tines which may be supplied with radio frequency energy in cyclic intervals to treat an area of tissue by advancing the individual electrode elements into the treatment region using an actuator mechanism which permits deployment of the tines in a desired three-dimensional configuration.

What is claimed:

1. An apparatus for treating tissue comprising:
   (a) an elongated member having a proximal end and a distal end;
   (b) a plurality of electrically insulated elongated inner tubes, shafts, or conduits contained within and axially traversing the elongated member: each of said inner tubes, shafts, or conduits comprising a lumen:
   (c) a plurality of elongated independent electrode tines, each electrode tine extending through said inner tubes, shafts, or conduits wherein each said inner tube, shaft, or conduit has a single electrode tine extending therethrough, and wherein each electrodes tine is longer than the elongated member;
   (d) said tines being insulated proximal to the proximal end of the elongated member;
   (e) the proximal end of each tine being connected to an energy source; and
   (f) an actuator mechanism being connected to a segment of each tine;
   wherein said energy source is an active rotating electrode which provides radio frequency energy in cyclic intervals.

2. The apparatus of claim 1 wherein the active rotating electrode is uniformly cycled among the tines.

3. The apparatus of claim 1 wherein the active rotating electrode contacts the terminal end of at least one tine for a longer duration than another tine.

4. The apparatus of claim 1 wherein the active rotating electrode comprises a single node.

5. The apparatus of claim 1 wherein the active rotating electrode comprises a dual node.

6. The apparatus of claim 1 wherein the active rotating electrode comprises a multiple node.

7. An apparatus for treating tissue comprising:
   (a) an elongated member having a proximal end and a distal end;
   (b) a plurality of electrically insulated elongated inner tubes, shafts, or conduits contained within and axially traversing the elongated member; each of said inner tubes, shafts, or conduits comprising a lumen;
   (c) a plurality of elongated independent electrode tines, each electrode tine extending through said inner tubes, shafts, or conduits wherein each said inner tube, shaft, or conduit has a single electrode tine extending therethrough, and wherein each electrodes tine is longer than the elongated member;
   (d) said tines being insulated proximal to the proximal end of the elongated member;
   (e) the proximal end of each tine being connected to an energy source; and
   (f) an actuator mechanism being connected to a segment of each tine;
   wherein the elongated member has apertures which extend axially along the exterior wall of the elongated member into each of said inner tubes, shafts, or conduits; and said actuator mechanism being configured and dimensioned to axially move each tine independently to extend beyond the distal end of the elongated member or to retract each tine within said elongated member.

8. The apparatus of claim 7 which the actuator mechanism comprises a number of side members, wherein each side member is connected to an individual tine through said apertures.

9. The apparatus of claim 8 in which said side members are solid arms attached to said tines at a substantially perpendicular angle.

10. The apparatus of claim 9 wherein said arms are manually pushed or pulled to extend or retract each individual tine from the distal end of the elongated member.

11. An apparatus for treating tissue with radio-frequency energy comprising:
   (a) an elongated member comprising a proximal end and a distal end;
   (b) a plurality of electrically insulated elongated inner tubes, shafts, or conduits contained within and axially traversing the elongated member; each of said inner tubes, shafts, or conduits comprising a lumen;
   (c) a plurality of elongated independent electrode tines, each electrode tine extending through said inner tubes, shafts, or conduits wherein each said inner tube, shaft, or conduit has a single electrode tine extending therethrough, and wherein each tine can be independently extended or retracted;
   (d) the proximal end of each tine being connected to an independent electrode element in a radio-frequency distributor in which said elements are periodically contacted by an active rotating electrode which provides radio frequency energy in cyclic intervals; and
   (e) an actuator mechanism being connected to a segment of each tine.

12. The apparatus of claim 11 wherein each tine is configured and dimensioned such that the distal ends of each tine substantially conform to an outwardly everted configuration when extended beyond the distal end of said elongated member and in a radially constrained configuration when axially retracted back within said elongated member.

13. The apparatus of claim 11 wherein the active rotating electrode comprises a single node.

14. The apparatus of claim 11 wherein the active rotating electrode comprises a dual node.

15. The apparatus of claim 11 wherein the active rotating electrode comprises a multiple node.

16. A method for treating tissue with radio-frequency energy using the apparatus of claim 11 comprising the steps of:
   (a) inserting the distal end of the elongated member into an area of tissue to be treated;

(b) extending or retracting the electrode tines to a desired position
(c) establishing a flow of radio-frequency energy to each tine independently in cyclic intervals.

17. The method of claim 16 wherein the velocity of the active rotating electrode is from about 10 cycles/second to about 100 cycles/second.

18. The method of claim 16 wherein the active rotating electrode is selected from the group consisting of a single node design, a double node design, or a multiple node design.

19. The method of claim 16 wherein the area of tissue to be treated is a tumor.

20. The method of claim 19 wherein the tumor is a malignant hepatic tumor.

21. The method of claim 16 wherein the distal end of elongated member is inserted into the area of tissue to be treated by first percutaneously inserting an obturator/stylet and sheath assembly, removing the obturator/stylet from the sheath to provide an access lumen, and then inserting the elongated member through the access lumen.

22. A method for treating tissue using an apparatus, the apparatus having an elongated member having a proximal end and a distal end; a plurality of electrically insulated elongated inner tubes, shafts, or conduits contained within and axially traversing the elongated member: each of said inner tubes, shafts, or conduits comprising a lumen; a plurality of elongated independent electrode tines, each electrode tine extending through said inner tubes, shafts, or conduits wherein each said inner tube, shaft, or conduit has a single electrode tine extending therethrough, and wherein each electrodes tine is longer than the elongated member; said tines being insulated proximal to the proximal end of the elongated member; the proximal end of each tine being connected to an energy source; and an actuator mechanism being connected to a segment of each tine, the method comprising the steps of:
   (a) inserting the distal end of the elongated member into an area of tissue to be treated;
   (b) independently extending or retracting each electrode tine to a desired position by moving the actuator mechanism of each tine: and
   (c) supplying energy to each tine from the energy source connected to the proximal end of each tine;
   wherein the energy comprises radio frequency energy that is supplied to each tine independently in cyclic intervals.

23. The method of claim 22 wherein the energy source comprises a distributor with an active rotating electrode.

24. The method of claim 23 wherein the velocity of the active rotating electrode is from about 1 cycles/second to about 100 cycles/second.

25. The method of claim 24 wherein the active rotating electrode is uniformly cycled among the tines.

26. The method of claim 24 wherein the active rotating electrode contacts the terminal end of at least one tine for a longer duration than another tine.

27. The method of claim 23 wherein the active rotating electrode is selected from the group consisting of a single node design, a double node design, or a multiple node design.

28. The method of claim 22 wherein the area of tissue to be treated is a tumor.

29. The method of claim 28 wherein the tumor is a malignant hepatic tumor.

30. The method of claim 29 wherein the tines are deployed and positioned to substantially cover the entire volume, area, and shape of the tumor.

31. The method of claim 22 wherein the distal end of elongated member is inserted into the area of tissue to be treated by first percutaneously inserting an obturator/stylet and sheath assembly, removing the obturator/stylet from the sheath to provide an access lumen, and then inserting the elongated member through the access lumen.

* * * * *